United States Patent
Tribus et al.

(10) Patent No.: US 6,461,359 B1
(45) Date of Patent: Oct. 8, 2002

(54) SPINE STABILIZATION DEVICE

(75) Inventors: Clifford B. Tribus, Madison, WI (US); Yves Crozet, Ramsey; William J. Kelly, Montville, both of NJ (US)

(73) Assignee: Clifford Tribus, Madison, WI (US)

( * ) Notice: Subject to any disclaimer, the term of this patent is extended or adjusted under 35 U.S.C. 154(b) by 0 days.

(21) Appl. No.: 09/437,391

(22) Filed: Nov. 10, 1999

(51) Int. Cl.[7] .............................................. A61B 17/70
(52) U.S. Cl. ...................... 606/61; 623/17.16
(58) Field of Search ............................ 606/61, 71, 69, 606/70; 623/17.15, 17.16, 17.11

(56) References Cited

U.S. PATENT DOCUMENTS

| 4,401,112 A | * | 8/1983 | Rezaian ..................... 128/92 B |
|---|---|---|---|
| 4,611,581 A | | 9/1986 | Steffee |
| 4,743,256 A | | 5/1988 | Brantigan |
| 4,759,709 A | | 7/1988 | Luken, Jr. et al. |
| 4,759,769 A | | 7/1988 | Hedman et al. |
| 5,062,850 A | * | 11/1991 | MacMillan et al. ........... 623/17 |
| 5,217,497 A | | 6/1993 | Mehdian |
| 5,258,031 A | | 11/1993 | Salib et al. |
| 5,314,477 A | | 5/1994 | Marnay |
| 5,458,641 A | * | 10/1995 | Ramirez-Jimenez ......... 623/17 |
| 5,458,642 A | | 10/1995 | Beer et al. |
| 5,522,899 A | | 6/1996 | Michelson |
| 5,554,191 A | | 9/1996 | Lahille et al. |
| 5,562,738 A | | 10/1996 | Boyd et al. |
| 5,645,599 A | | 7/1997 | Samani |
| 5,653,763 A | | 8/1997 | Errico et al. |
| 5,674,296 A | | 10/1997 | Bryan et al. |
| 5,679,296 A | | 10/1997 | Kelman et al. |
| 5,713,899 A | | 2/1998 | Marney et al. |
| 5,766,252 A | | 6/1998 | Henry et al. |
| 5,779,707 A | * | 7/1998 | Bertholet et al. ............. 606/75 |
| 5,782,831 A | | 7/1998 | Sherman et al. |
| 5,800,433 A | | 9/1998 | Benzel et al. |
| 5,814,046 A | | 9/1998 | Hopf |
| 5,885,299 A | | 3/1999 | Winslow et al. |
| 5,888,223 A | | 3/1999 | Bray, Jr. |
| 5,895,428 A | | 4/1999 | Berry |
| 5,899,901 A | | 5/1999 | Middleton |
| 6,106,557 A | * | 8/2000 | Robioneck et al. ........... 623/17 |
| 6,156,037 A | * | 12/2000 | LeHuec et al. ............... 606/61 |
| 6,224,599 B1 | * | 5/2001 | Baynham et al. ............ 606/61 |
| 6,228,085 B1 | * | 5/2001 | Theken et al. ................ 606/61 |

FOREIGN PATENT DOCUMENTS

| EP | 0974319 | 1/2000 |
|---|---|---|
| EP | 0179695 | 9/2000 |
| WO | WO 97/20526 | 6/1997 |
| WO | WO 97/37620 | 10/1997 |
| WO | WO 98/04202 | 2/1998 |
| WO | WO 98/04217 | 5/1998 |
| WO | WO 99/27864 | 6/1999 |

* cited by examiner

*Primary Examiner*—Eduardo C. Robert
(74) *Attorney, Agent, or Firm*—Foley & Lardner

(57) ABSTRACT

A spine stabilization device is placed between adjacent vertebral bodies of the vertebrae of a spine to maintain a desired orientation and spacing between the adjacent vertebral bodies and support the adjacent vertebral bodies for fusion at the desired orientation and spacing. The stabilization device includes a plate adapted for fixation to the sides of adjacent vertebral bodies, and at least two legs attached to the plate which are adapted for disposal between the adjacent vertebral bodies to provide support therebetween, there being a space between two of the legs such that together with the plate a U shape is formed as viewed superior to inferior.

22 Claims, 5 Drawing Sheets

SPINE STABILIZATION DEVICE

FIELD OF THE INVENTION

The present invention relates generally to the stabilization or immobilization of vertebral bodies in the spinal column, as well as methods and instruments for achieving same.

BACKGROUND OF THE INVENTION

The spinal column of humans provides support for the body and protection to the delicate spinal cord and nerves. The spinal column comprises a series of vertebrae stacked on top of each other. Each vertebra has a relatively large vertebral body located in the anterior portion of the spine and provides the majority of the weight bearing support of the vertebral column. Each vertebral body has relatively strong bone comprising the outside surface of the body (cortical) and relatively weak bone comprising the center of the body (cancellous). Situated between each vertebral body is an intervertebral disc, which provides for cushioning and dampening of compressive forces to the spinal column. Located just posterior to the vertebral body and intervertebral disc is the vertebral canal containing the delicate spinal cord and nerves. Posterior to the spinal canal are the different articulating processes of the vertebra.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain and often neurologic deficit.

Spinal fusion is a technique often utilizing surgical implants which mechanically immobilize areas of the spine with eventual incorporation of grafting material. Such techniques have been used effectively to treat the above-described conditions and, in most cases, to relieve pain suffered by the patient. However, there are some disadvantages to the present fixation devices.

One technique for spinal fixation includes immobilization of the spine by the use of spine rods that run generally parallel to the spine. In practicing this technique, the posterior surface of the spine is exposed, and bone screws are first fastened to the pedicles of the appropriate vertebrae or to the sacrum, acting as anchor points for the spine rods. The bone screws are generally placed two per vertebrae, one at each pedicle on either side of the spinous process. Clamp assemblies join the spine rods to the screws. The spine rods are generally bent to achieve the desired curvature of the spinal column. Such systems are very stable but require implanting screws into each vertebrae to be treated. Also, since the pedicles of vertebrae above the second lumbar vertebra (L2) are very small, only small bone screws can be used, which sometimes do not give the needed support to stabilize the spine. To stabilize the unstable spine sufficiently, one to two vertebrae above and one to two vertebrae below the area to be treated are often used for implanting the screws. The rods and clamps are surgically fixed to the spine from a posterior approach.

Anterior fixation devices have also been used, such as anterior plate systems. One type of anterior plate system involves a titanium plate with unicortical titanium bone screws that lock to the plate and are placed over the anterior surface of the vertebral body. Another type of anterolateral plate system used less frequently involves the use of bicortical screws that do not lock to the plate. The bone screws have to be long enough to bite into both sides of the vertebral body to gain enough strength to obtain the needed stability. These devices are difficult to place due to the length of the screws, and damage occurs when the screws are misplaced.

A third type of anterior fixation device comprises a hollow device that may or may not be externally threaded. The device is positioned between two adjacent vertebral bodies. Bone grafts from cadavers or from the pelvic region of the patient may be placed into the hollow center of the device. Bone morphogenic protein or other substances that promote bone growth can also be placed into the hollow center of the device. The cage might allow bone to grow through the device and fuse the two adjacent vertebrae.

Although the devices described above present various solutions, further improvement in this area is desirable. There remains a need to have a stabilization device which connects to the strong vertebral bodies. The device should be easy to place and should prevent potentially damaging telescoping of adjacent vertebrae.

SUMMARY OF THE INVENTION

The present invention overcomes the drawbacks in the prior art by providing a stabilization device having greater intrinsic stability. The present invention also overcomes drawbacks associated with the prior art by providing a stabilization device which can restore the proper height between adjacent vertebrae in one implant. Moreover, the stabilization device of the present invention may provide a greater area of space for bone grafts.

One aspect of the present invention provides a stabilization device. The stabilization device includes a plate adapted for fixation to the sides of adjacent vertebral bodies. The device also includes at least two legs attached to the plate which are adapted for disposal between the adjacent vertebral bodies to provide support therebetween. There is a space between two of the legs such that together with the plate a U shape is formed as viewed superior to inferior. Preferably, the legs extend along the plane which is transverse to the plane of the plate. More preferably, the legs extend along a plane which is substantially perpendicular to the plane of the plate.

Another aspect of the present invention provides a method of stabilizing adjacent vertebral bodies. The method includes the steps of: providing a stabilization device having at least two legs and a bridging member connecting the legs to define an approximate U-shape as viewed superior to inferior; inserting the stabilization device between the adjacent vertebral bodies such that the legs extend in a direction between anterior and posterior; and fixing the stabilization device by inserting at least one fixation device into the anterior or posterior face of at least one of the adjacent vertebral bodies. Preferably, the method also includes the step of inserting a fixation member along the legs. In a more preferred embodiment, the legs may include a recess extending in a direction between anterior and posterior. The method may further include the step of inserting a leg fixation member within the recess such that the leg fixation member is partly in at least one of the adjacent vertebral bodies and partly in the recess along the axis of said leg.

In yet another aspect of the invention, a stabilization device is provided that includes an intervertebral body adapted for positioning between adjacent vertebral bodies. The intervertebral body has a first end and a second end, and a first surface and a second surface for contacting the respective surfaces of the vertebral bodies. The stabilization device also includes a fixation member adapted to fix the intervertebral body to one of the adjacent vertebral bodies. The fixation member is sized so that when positioned for fixation, a portion of the member extends beyond the first surface of the intervertebral body and engages the bone of the vertebral body. In a preferred embodiment, no portion of the fixation member extends beyond the second surface of the intervertebral body.

In preferred embodiments, the stabilization device may also include a channel formed in at least one of the first and second surfaces of the intervertebral body. The channel may extend between the first and second ends of the intervertebral body. In a more preferred embodiment, the stabilization device may further include a fixation member having a width, which when positioned for fixation, is partially in one of the vertebral bodies, the remaining portion being exterior to the vertebral bodies, preferably within the intervertebral body. Preferably, at least about 25% of the width of the fixation member is in one of the vertebral bodies. Most preferably, when positioned for fixation, about 25% to about 50% of the width of the fixation member is in one of the vertebral bodies. Of course, the fixation member can be in one of the vertebral bodies outside of this range.

In an alternative embodiment, the stabilization device may include a plate attached to the intervertebral body. The plate may be adapted for fixation to the anterior, lateral or posterior sides of at least one of the adjacent vertebral bodies. In a preferred embodiment, the plate is adapted for fixation to the anterior or lateral sides of both of the adjacent vertebral bodies. In a most preferred embodiment, the plate is adapted for fixation the anterior side of both of the adjacent vertebral bodies.

In a further aspect of the invention, a method is provided for stabilizing adjacent vertebral bodies. The method includes inserting an intervertebral body between the adjacent vertebral bodies. The intervertebral body has a first end and a second end, and a first surface and a second surface, which contact the respective surfaces of the vertebral bodies. The method also includes inserting at least one fixation member which is sized so that a portion of the fixation member extends beyond the first surface of the intervertebral body and engages the bone of one of the vertebral bodies. In a preferred embodiment, no portion of the fixation member extends beyond the second surface of the intervertebral body. More preferably, when the fixation member is positioned for fixation, the fixation member is partially in one of the vertebral bodies, the remaining portion being exterior to the vertebral bodies, preferably within the intervertebral body. Preferably, at least about 25% of the width of the fixation member is in one of the vertebral bodies. Most preferably, about 25% to about 50% of the width of said fixation member is in one of the vertebral bodies and the remaining width of said fixation member is within said intervertebral body. Of course, the fixation member can be in one of the vertebral bodies outside of this range.

In a preferred embodiment, the method may also include inserting an intervertebral body having a channel formed in at least one of the first and second surfaces. The channel may extend between the first and second ends of the intervertebral body.

In another preferred embodiment, the method further includes the step of affixing a plate, which is attached to the intervertebral body, to the anterior, lateral or posterior side of at least one of the adjacent vertebral bodies. More preferably, the plate is affixed to the anterior or lateral sides of both of the adjacent vertebral bodies. Most preferably, the plate is affixed to the anterior side of both of the adjacent vertebral bodies.

A further aspect of the invention provides a stabilization device that includes an intervertebral body adapted for positioning between adjacent vertebral bodies. The intervertebral body has a first end and a second end, and a first surface and a second surface for contacting the respective surfaces of the vertebral bodies. The intervertebral body is constructed and arranged to allow the stabilization device to flex superiorly and inferiorly when arranged between the vertebral bodies and prior to fusion of the vertebral bodies. In a preferred embodiment, the stabilization device includes a slot extending transversely in a direction between anterior and posterior to allow the stabilization device to flex superiorly and inferiorly when arranged between the vertebral bodies and prior to fusion of the vertebral bodies.

In an alternative embodiment, the stabilization device may include a plate adapted for fixation to the anterior, lateral or posterior sides of the adjacent vertebral bodies. The device may also include legs extending transversely from the plate such that there is a space between the legs. The legs extend with the sides of said plate to form an approximate U-shaped device. The legs may also include a slot extending transversely in a direction between anterior and posterior to allow the stabilization device to flex superiorly and inferiorly when arranged between the vertebral bodies and prior to fusion of the vertebral bodies.

In another alternative embodiment, the device may include a plate adapted for fixation to the anterior, lateral or posterior sides of the adjacent vertebral bodies. The device may further include legs extending transversely from the plate such that there is a space between the legs. The legs may extend with the sides of the plate to form an approximate U-shaped device. Further, the legs may be of different elasticity than the plate to allow the stabilization device to flex superiorly and inferiorly when arranged between the vertebral bodies and prior to fusion of the vertebral bodies. In a preferred embodiment, the legs are formed from polyethylene ether ketone (PEEK).

In yet a further aspect of the invention, a method is provided for stabilizing adjacent vertebral bodies. This method includes the step of inserting a stabilization device between adjacent vertebral bodies. The stabilization device has a first end and a second end, and a first surface and a second surface for contacting the respective surfaces of the vertebral bodies. The stabilization device is constructed and arranged to allow the stabilization device to flex superiorly and inferiorly when arranged between the vertebral bodies and prior to fusion of the vertebral bodies. In a preferred embodiment, the method may include inserting a stabilization device having a slot extending transversely in a direction between anterior and posterior to allow the stabilization device to flex superiorly and inferiorly when arranged between the vertebral bodies and prior to fusion of the vertebral bodies. In certain preferred embodiments, the method may include inserting a stabilization device that has a plate adapted for fixation to the anterior, lateral or posterior sides of adjacent vertebral bodies. The legs may extend transversely from the plate such that there is a space between the legs. The legs may also extend with the sides of the plate to form an approximate U-shaped device. In addition, the legs may include a slot extending transversely in a direction between anterior and posterior to allow the stabilization device to flex superiorly and inferiorly when arranged between the vertebral bodies and prior to fusion of the vertebral bodies.

In an alternative embodiment, the legs are of different elasticity than the plate to allow the stabilization device to flex superiorly and inferiorly when arranged between the vertebral bodies and prior to fusion of the vertebral bodies. In a preferred embodiment, the legs are formed from polyether ether ketone (PEEK).

A further aspect of the invention provides a modular stabilization device. The device includes a plate adapted for fixation to the anterior, lateral or posterior sides of adjacent vertebral bodies. The plate has a front face and a back face. The device also includes a separate stabilization member that has a first surface and a second surface for contacting the respective surfaces of the vertebral bodies. When the separate stabilization member is affixed to the back face of the plate, it extends along a plane which is substantially perpendicular to the plane of the plate.

A further aspect of the invention provides a method for reducing a displaced vertebra in the spine. The method includes providing a stabilization device having a plate adapted for fixation to the sides of adjacent vertebral bodies. The legs are adapted for disposal between the adjacent vertebral bodies to provide support therebetween. There is a space between the legs such that the legs and the plate together define an approximate U-shape as viewed superior to inferior. The stabilization device is positioned between a first vertebral body, which is in proper alignment with the remaining vertebral bodies, and a second vertebral body, which is not in proper alignment with the remaining vertebral bodies. The device is attached to the first vertebral body. The second vertebral body is then reduced by translating the second vertebral body so that it is in alignment with the first vertebral body. Finally, the device is attached to the second vertebral body.

In another aspect of the invention, a kit is provided that includes at least one plate adapted for fixation to the anterior, lateral or posterior sides of adjacent vertebral bodies. The plate has a front face and a back face, and a plurality of separate and different stabilization members attachable to the plate. The stabilization members have a first surface and a second surface for contacting the respective surfaces of the vertebral bodies, which when affixed to the back face of said plate extends along a plane which is transverse to the plane of the plate.

Alternatively the kit may include a plurality of separate and different plates adapted for fixation to the anterior, lateral or posterior sides of adjacent vertebral bodies, said plates having a front face and a back face, and at least one stabilization member having a first surface and a second surface for contacting the respective surfaces of the vertebral bodies, which when affixed to the back face of the plate extends along a plane which is transverse to the plane of the plate.

In an alternative embodiment, the kit may include multiple sized and shaped plates and stabilization members.

In yet another aspect of the invention, an apparatus is provided for use in manipulating a displaced vertebra in the spine. The apparatus includes a first extendable member for manipulating at least one vertebra, and a second extendable member cooperating with the first extendable member for manipulating at least one adjacent vertebra. Alternatively, the apparatus may also include a third extendable member which is slidably positioned between the first and second extendable members for distracting the adjacent vertebrae.

DETAILED DESCRIPTION OF THE PREFERRED EMBODIMENTS

Figure 1:
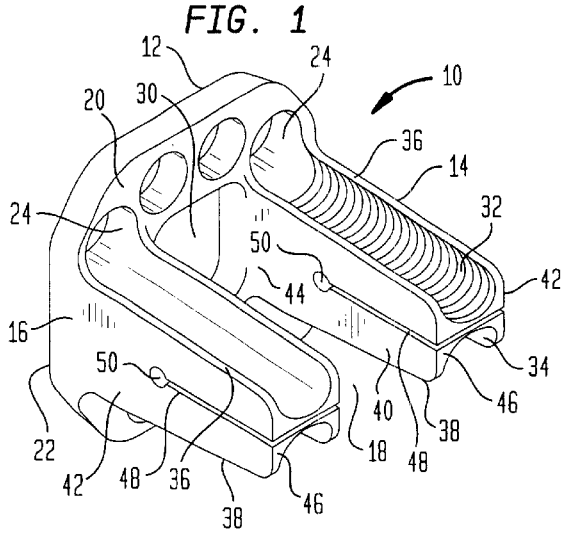
FIG. 1 is a rear perspective view of one embodiment of the present invention.

Referring to FIG. 1, a stabilization device in accordance with one embodiment of the present invention is generally designated as 10. The device, which is constructed of biocompatible material, includes a plate 12. The device 10 further includes legs 14 and 16 attached to plate 12. As shown in FIG. 1, the legs extend along a plane which is substantially perpendicular to the plane of the plate, there being a space 18 between the legs such that together with the plate 12 the legs form a U shape as viewed superior to inferior. However, it should be understood that the legs may extend in other planes with respect to the plane of the plate while still maintaining a generally U-shaped configuration. Of course, in other embodiments, a U shape may not be formed as other arrangements of the legs and plate are established. For example, one leg or three legs might be provided.

Figure 3:
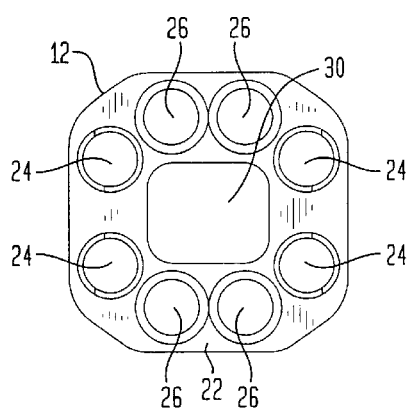
FIG. 3 is a front view of the embodiment of FIG. 1.
Figure 5:
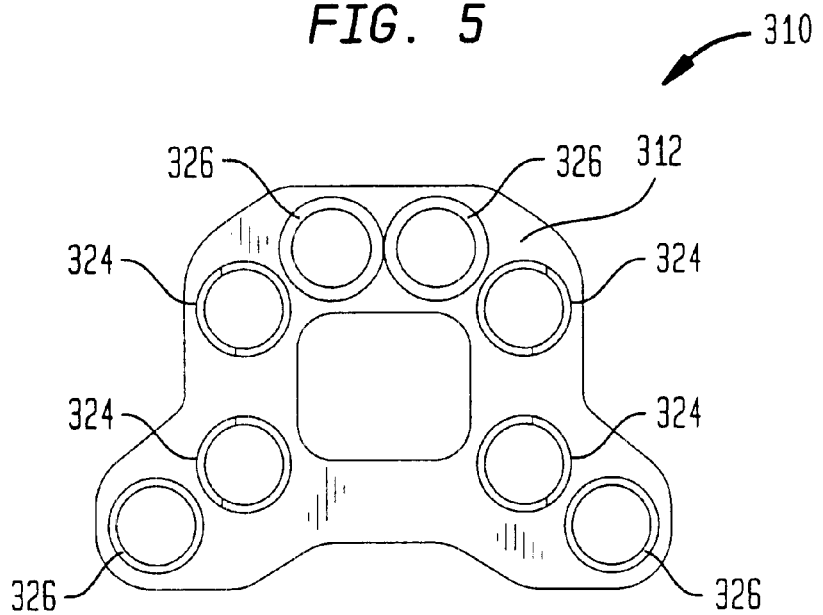
FIG. 5 is a front view of yet another embodiment of the present invention.

As best shown in FIGS. 1 and 3, plate 12 has an inner surface 20 which faces toward the vertebrae, and an outer surface 22 which faces away from the vertebrae. Plate 12 also includes through holes 24 and 26. Plate 12 may be octagonal in shape. However, the plate may be any shape, e.g., circular, square, hexagonal, etc., in alternate embodiments of the present invention. For example, as best shown in FIG. 5, plate 312 is shaped to facilitate fixation of the plate to the L-5 and S-1 vertebrae.

Figure 8:
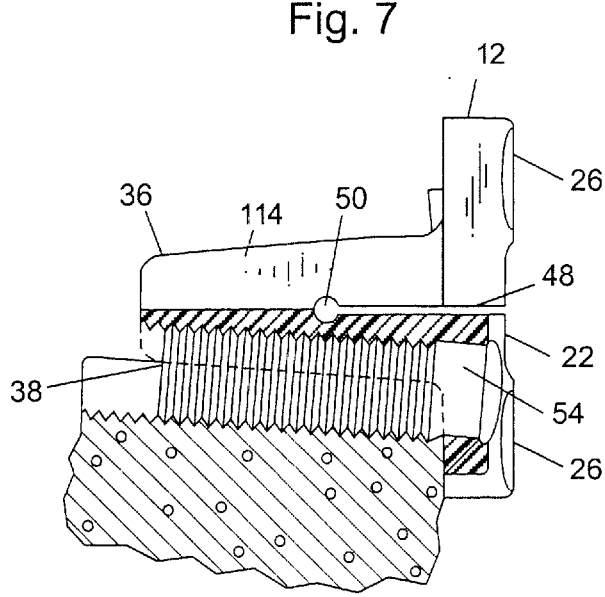
FIG. 8 is a cross-section view of yet another embodiment of the invention.

Through holes 24 are substantially symmetrically opposed between the top and bottom halves of plate 12. As seen in FIG. 1, through holes 24 extend from outer surface 22 to inner surface 20, terminating in line with channels 32 and 34 in leg 14. In FIG. 8, it can be seen that a fixation member 54 is inserted into through hole 24 to fix stabilization device 10 to a vertebral body, as will be discussed in detail below. Fixation member 54 may be any type of suitable fastener, such as an anchor, screw, dowel, etc. Preferably, fixation member 54 is a screw. More preferably, the screw has a threaded head which mates with threads in through holes 24 so as to threadedly connect the screw to plate 12. Alternatively, fixation member 54 is a polyaxial screw which permits the screw to be inserted at a variety of angles while still permitting the coupling element to be screwed into through hole 24 or through hole 26.

In a preferred embodiment, through holes 26 are positioned between through holes 24 on the top and bottom halves of plate 12. In an alternative embodiment, the bottom half through holes 26 are replaced with an opening, which can be a slot for reduction purposes as discussed below. Preferably, through holes 26 are not threaded so as to allow a surgeon greater control over the positioning of a fixation member inserted into through hole 26. Alternatively, through holes 26 and/or opening 28 could be identical to the through holes 24. The present invention is not limited to any particular configuration of the through holes 26.

Figure 2:
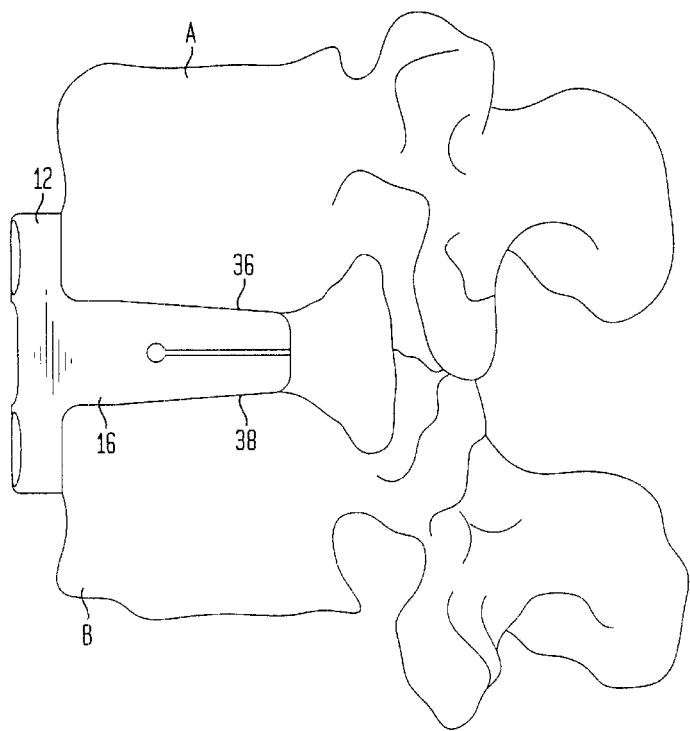
FIG. 2 is a side elevation view of the embodiment of FIG. 1.

In a preferred embodiment, plate 12 may further include an aperture 30, which provides access to space 18. Bone fragments, bone growth factors, other materials promoting the growth of bone, blood vessels or other tissue, or materials used in a reduction procedure may be packed into device 10 through aperture 30. In an alternative embodiment, plate 12 may not include aperture 30 or may include smaller apertures in place of a single aperture. In embodiments having no apertures at all, the device might be packed with any of the above materials prior to placement of device 10 between adjacent vertebrae A and B (FIG. 2).

As best shown in FIG. 1, legs 14 and 16 are attached to plate 12. In a preferred embodiment, the legs extend along a plane which is transverse to the plane of plate 12. More preferably, the legs extend along a plane which is substantially perpendicular to the plane of the plate. Of course, other configurations of the legs in relation to the plate are contemplated and within the scope of the invention. Legs 14 and 16 may not be substantially the same, but in the preferred embodiment they are. Therefore, the description of leg 14 may also apply to leg 16.

Leg 14 includes a first surface 36 and a second surface 38 for contacting the respective surfaces of adjacent vertebral bodies. The leg has sufficient strength and rigidity to maintain the vertebrae in a desired spatial relationship, as shown in FIG. 2. This may include a shaping and/or sizing of the leg. As shown, the leg tapers from larger to smaller from anterior to posterior, to more anatomically imitate the space that should be maintained between the vertebral bodies. However, it should be understood that other shapes may be used to maintain the desired spatial relationship between the vertebral bodies and still be within the scope of the invention.

The legs also have opposing inner surfaces 40 as well as outer surfaces 42 spaced apart laterally and extending longitudinally from a proximal end 44 to a distal end 46.

The legs may further include channels 32 and 34 which are substantially symmetrically opposed on the superior and inferior sides of leg 14. Preferably, the channels are cylinderical in shape. As best shown in FIGS. 1 and 8, the channels may be threaded and permit the insertion of a fixation member 54 into a vertebral body B. The channel may extend for substantially the entire length of the leg as shown in FIG. 1. However, it is contemplated that the channels need not extend the entire length of the leg, thus permitting a surgeon to insert the fixation member along axes not substantially parallel to the axis of the leg.

Preferably, fixation member 54 is sized so that when positioned for fixation, a portion of fixation member 54 extends beyond surface 38 of leg 14 and engages the bone of vertebral body B. No portion of fixation member 54 extends beyond surface 36 of leg 14 to engage the other vertebral body. The fixation member 54 engages only one of the vertebral bodies. In a preferred embodiment, at least about 25% of the width of fixation member 54 is in one of the vertebral bodies. In a more preferred embodiment, about 25% to about 50% of the width of fixation member 54 is in one of the vertebral bodies. Fixation members 54 and 56 are preferably comprised of titanium but may also be comprised of stainless steel, ceramics, composite materials, other materials known in the surgical and medical arts, and/or biologically inert materials may be used.

The legs may also include a flexing feature, which by structure or material permits device 10 to flex superiorly and inferiorly when arranged between the vertebral bodies and prior to fusion of the vertebral bodies. Preferably, this feature is facilitated by slot 48, which extends substantially parallel to the plane of the leg. More preferably, slot 48 extends from distal end 46 to a relief opening 50. Most preferably, slot 48 is also provided to extend from the inner surface 40 to outer surface 42. In an alternative embodiment, slot 48 extends longitudinally from the outer surface 22 of the plate to a relief opening 50 in leg 14, as shown in FIG.8. It is contemplated, however, that a slot extending from distal end 46 to relief opening 50 may provide greater flexibility to device 10. Other embodiments are also contemplated which would permit the device to flex. For example, a hinge of any suitable type might be constructed or materials of different elasticity might be used in the plate and legs. Plate 12 may be constructed of a metal, preferably titanium or stainless steel, while legs 14 and 16 may be constructed of a more pliable material such as polyethylene or polyether ether ketone ("PEEK"), polyurethane, carbon, hydroxyapetile, bone, or ultra high molecular weight polyethelene ("UHMWPE").

Figure 4:
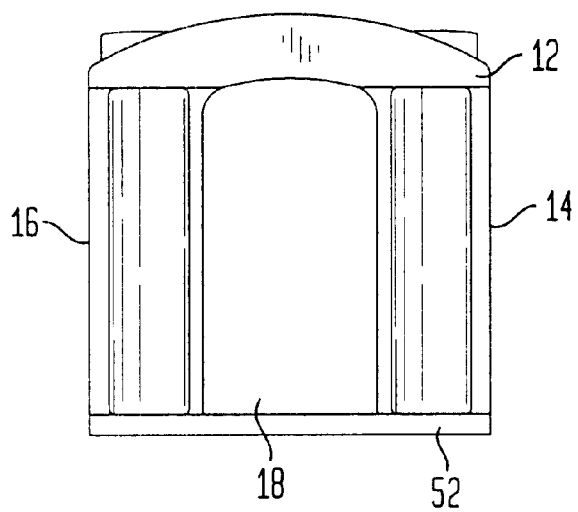
FIG. 4 is a top plan view of another embodiment of the present invention.

In an alternative embodiment, legs 14 and 16 may also include a bridging member 52 (as best seen in FIG. 4) to provide additional stability or support to device 10. The location of bridging member 52 in relation to legs 14 and 16 may be varied in alternative embodiments of the invention. Bridging member 52 can be at any position along the legs 14 and 16, but in one preferred embodiment the bridging member is positioned at the ends 46 of the legs 14 and 16. The bridging member or members may have the same height as the legs at its point of connection or may vary in height.

Figure 6:
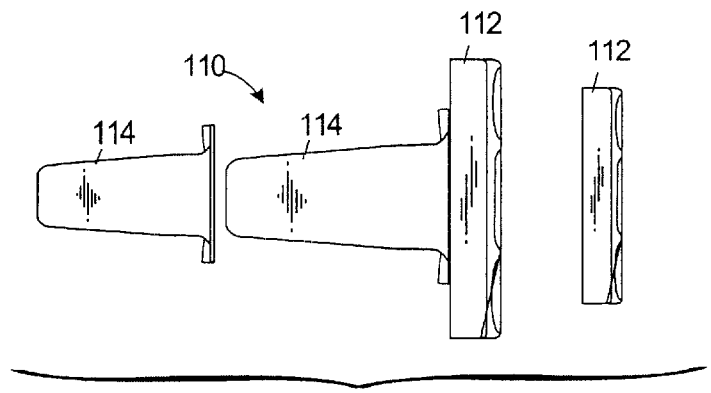
FIG. 6 is a side elevation view of a further embodiment of the present invention.

The stabilization device may be a modular unit 110 (FIG. 6) which permits the use of separate and different sized plates and legs to accommodate for the varying sizes of vertebral bodies. As best seen in FIG. 6, plate 112 and leg 114 may be separate components which are attached in any suitable manner, e.g., through the use of screws, anchors, expansion arms, dowels, etc., as well as means developed in the future. Thus, a surgeon who is performing an anterior fixation surgery can isolate the spine using well known surgical techniques and place an appropriate sized and shaped plate and legs from the kit into the intervertebral space of two adjacent vertebrae. If the legs or plate are too large or too small, the plate or legs can be removed and replaced with a plate or legs of a more appropriate size and shape.

As discussed above, stabilization device 10 is placed either anteriorly, laterally or posteriorly between adjacent vertebrae of a spine and seated upon confronting end plates of the adjacent vertebral bodies to maintain a desired orientation and spacing between the adjacent vertebral bodies. The device may also support the adjacent vertebral bodies for fusion at the desired orientation and spacing in the treatment of patients with spondylolisthesis, ruptured, or otherwise degenerative intervertebral discs. In a preferred embodiment, stabilization device 10 is inserted anteriorly or laterally. More preferably, stabilization device 10 is inserted anteriorly.

If stabilization device 10 is to be inserted anteriorly, a patient needing spinal fixation or fusion will be prepped appropriately for anterior spine surgery. The surgeon would then use standard anterior surgical approaches to isolate two or more vertebral bodies to be treated. The intervertebral disc would then be removed and a curette or similar surgical instrument would be used to prepare the vertebral bodies and plates for receiving the anterior fixation device.

The surgeon then selects an appropriate stabilization device 10 and inserts the device between the adjacent vertebral bodies such that the legs extend in a direction between anterior and posterior. Once the stabilization device 10 is properly placed between adjacent vertebral bodies, the surgeon next secures the stabilization device 10 to the adjacent vertebrae by inserting at least one fixation member along legs 14 and 16 of stabilization device 10.

Space 18 between legs 14 and 16 is then filled with bone grafts, bone morphogenic protein, or the like, through aperture 30 of plate 12. Alternatively, if plate 12 does not include aperture 30, space 18 between legs 14 and 16 may be filled with bone grafts, bone morphogenic protein or the like before placement of stabilization device 10 in the intervertebral disc space.

Once the spinal column has been appropriately treated, the surgeon then finishes the anterior surgery using well-known surgical techniques.

Figure 7:
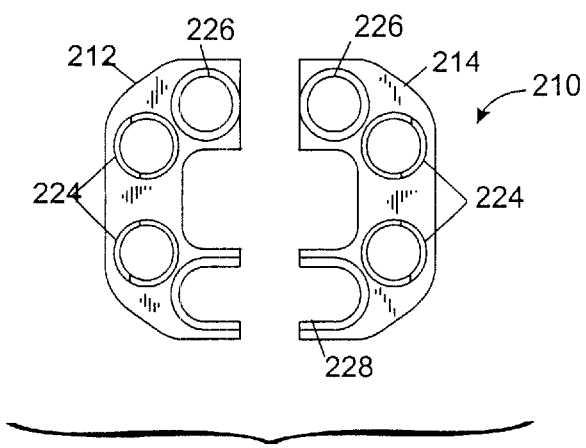
FIG. 7 is a front view of another embodiment of the invention.

If the device is inserted posteriorly, it is contemplated that a stabilization device as best shown in FIG. 7 may be useful. In this embodiment, stabilization device 210 comprises at least two separate plates 212 and 214 to more easily approach the vertebrae while avoiding blood vessels and other tissues that may be blocking access to the vertebrae. The surgeon will use common posterior surgical techniques to expose the vertebrae for insertion of stabilization device 210. To avoid surrounding vessels and other tissues, the surgeon would insert plate 212 (and corresponding leg) on one side of the vertebrae and insert plate 214 (and its corresponding leg) from the other side. Plates 212 and 214 would then be attached to each other by well-known attaching means. The device is then fixed to the adjacent vertebral bodies as discussed above by exerting fixation members through holes 224 and 226. As shown in FIG. 7, through holes 226 may be replaced with a slot 228 therein.

Figure 9A:
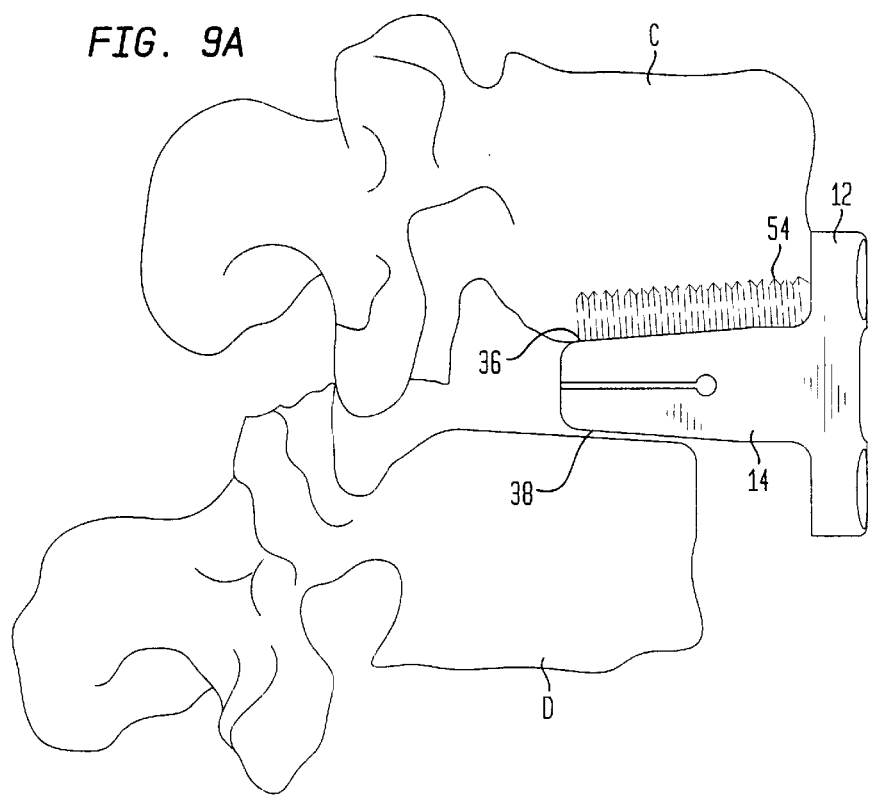
FIGS. 9A and 9B are side elevation views illustrating the use of the embodiment of FIG. 1.
Figure 9B:
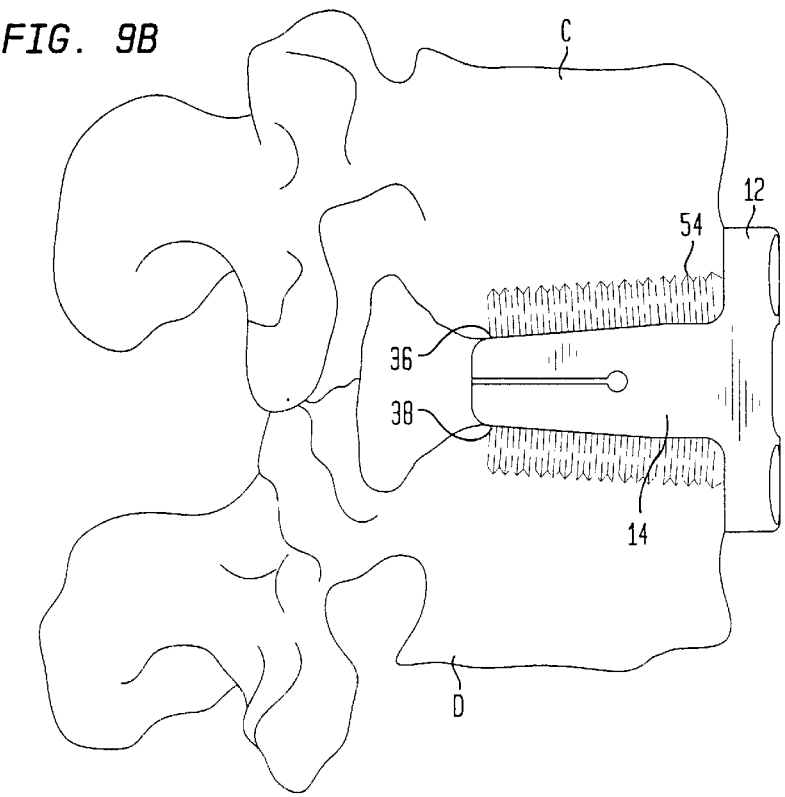

If the surgeon is required to reduce a misaligned vertebral body (for example, as shown in FIGS. 9A and 9B), the surgeon first will prep a patient appropriately and use standard surgical approaches to isolate the vertebral bodies to be treated. For example, distraction wedges may be placed into the disc space serially distracting (overdistracting) as far as the soft tissues will allow. If, for example, the stabilization device is to be inserted into the L5-S1 interspace, plate 310 (FIG. 5) may be used. Fixation members may be inserted into through holes 324 and 326 on the top half of the plate to fix stabilization device 310 to the L5 vertebrae. Fixation members would then be inserted into through holes 326 on the bottom half of the plate and slowly advanced, thereby drawing the S1 body to the plate 312 and affecting the reduction. Fixation members are then inserted into through holes 324 on the bottom half of the plate, thus securing stabilization device 310 to the S1 end plate.

Figure 10:
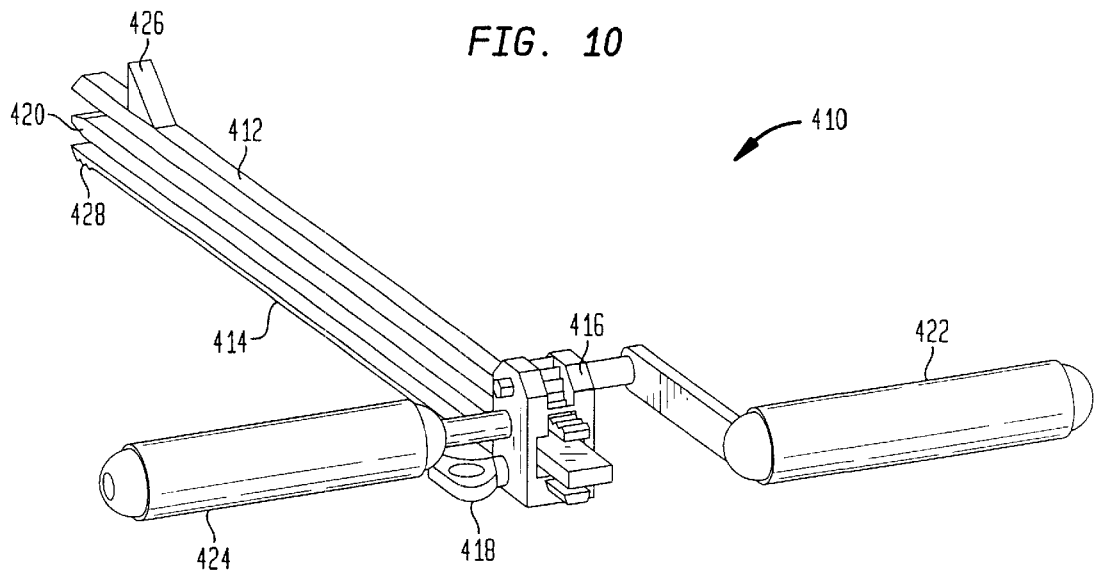
FIG. 10 is a perspective view of a reduction apparatus according to an embodiment of the invention for use in connection with any of the embodiments depicted in FIGS. 1–9.

As best shown in FIG. 10, an appropriate tool ("reduction apparatus") 410 may be used to move a misaligned vertebra into alignment with the adjacent vertebrae. Tool 410 includes a ratcheting device 416 having handles 422 and 424 attached thereto. Tool 410 also includes vertebral displacement rods 412 and 414, which are engaged by ratchet 416. The rods may also include teeth 428 which are capable of frictionally engaging the vertebral bodies. Vertebral displacement rod 412 may also include a finger 426 which is capable of engaging a vertebra. A distraction wedge 420 is slidably positioned between vertebral displacement rods 412 and 414. Tool 410 further includes a fastener 418 which when inserted into ratchet 416 engages vertebral displacement rod 414 to prevent displacement rod 414 from slidably moving within ratchet 416.

Figure 11:
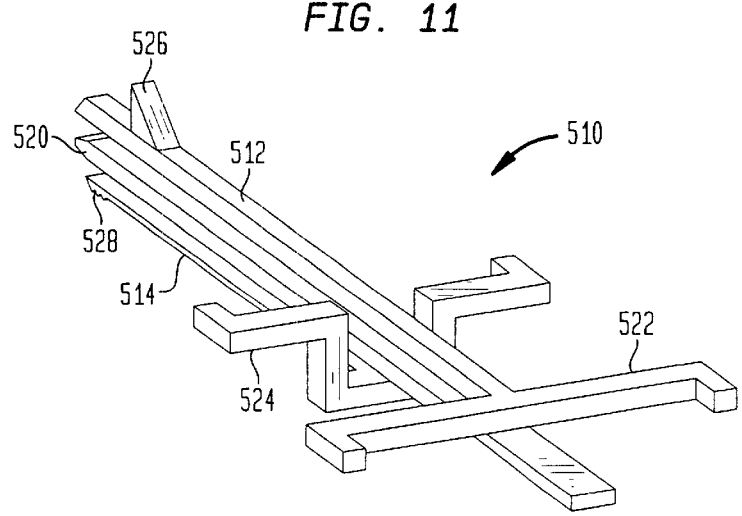
FIG. 11 is a perspective view of another reduction apparatus according to a further embodiment of the invention for use in connection with any of the embodiments depicted in FIGS. 1–9.

In an alternative embodiment, tool 510 (FIG. 11) may be used to move a misaligned vertebra. Tool 510 includes vertebral displacement rods 512 and 514. Vertebral displacement rod 512 includes a handle 522 attached thereto. Vertebral displacement rod 512 may also include a finger 526 capable of engaging a vertebral body. Vertebral displacement rod 514 includes a handle 524 and may include teeth 528 which are capable of frictionally engaging a vertebral body. A distraction wedge 520 is slidably positioned between vertebral displacement rods 512 and 514 to distract adjacent vertebrae.

The surgeon prepares a patient as discussed above, including overdistracting the disc space. Stabilization device 10 is then inserted into the disc space. Vertebral displacement rods 412 and 414 are inserted through aperture 30 of stabilization device 10. Ratcheting device 416 is mounted over vertebral displacement rods 412 and 414. Vertebral displacement rod 414 is then locked in place using fastener 418. Teeth 428 on vertebral displacement rod 414 are then impacted in the endplate of a vertebral body. Distraction wedge 420 is then inserted between vertebral displacement rods 412 and 414 through ratcheting device 416 to distract the disc space. Handle 422 is then turned, which engages vertebral displacement rod 412 in ratcheting device 416 to translationally move vertebral displacement rod 412 from anterior to posterior, thereby causing finger 426 to push the superior vertebra posteriority to a more desired position. Stabilization device 10 is then fixed to the vertebral bodies by inserting fixation members as described above. The surgeon may then remove ratcheting device 416, wedge 420 and displacement rod 412 and 414.

Tool 510 may be used in place of tool 410. Vertebral displacement rods 512 and 514 are inserted through aperture 30 of stabilization device 10, similar to the method described above for tool 410. Teeth 528 on vertebral displacement rod 514 are then impacted in the endplate of a vertebral body. Distraction wedge 520 is inserted between vertebral displacement rods 512 and 514 to distract the discs. Handles 522 and 524 are subsequently compressed to translationally move rod 512 from anterior to posterior and rod 514 from posterior to anterior, thus aligning the two vertebrae.

As these and other variations and combinations of the features discussed above can be utilized without departing from the invention as defined by the claims, the foregoing description of the preferred embodiments should be taken by way of illustration rather than by way of limitation of the invention.

We claim:

1. A method of stabilizing adjacent vertebral bodies each having an anterior, lateral and posterior face, comprising the steps of:

(a) providing a stabilization device having at least two legs and a bridging member connecting the legs to define a U shape as viewed superior to inferior;

(b) inserting the stabilizing device between the adjacent vertebral bodies such that the legs extend in a direction between anterior and posterior;

(c) inserting a leg fixation member along the legs; and (d) fixing the stabilization device by inserting at least one fixation device into the anterior, lateral or posterior face of at least one of the adjacent vertebral bodies, wherein the step of providing a stabilization device includes a stabilization device having legs which include a recess extending in a direction between anterior and posterior, and wherein the step of inserting a leg fixation member comprises inserting the leg fixation member within the recess such that the leg fixation member is partly in at least one of the adjacent vertebral bodies and partly in the recess of the leg.

2. A stabilization device comprising:

(a) an intervertebral body adapted for positioning between adjacent vertebral bodies, each vertebral body having a surface, said intervertebral body having a first end and a second end, and a first surface and a second surface for contacting the respective surfaces of the vertebral bodies, and further comprising a channel formed in at least one of said first and second surfaces of said intervertebral body; and (b) a fixation member adapted to fix said intervertebral body to one of the adjacent vertebral bodies, said fixation member being sized so that when positioned for fixation a portion of said fixation member extends beyond said first surface of said intervertebral body and engages the bone of the vertebral body, and wherein no portion of said fixation member extends beyond said second surface of said intervertebral body.

3. The stabilization device of claim 2, wherein said channel extends between said first end and said second end of said intervertebral body.

4. The stabilization device of claim 2, wherein said fixation member has a width and when positioned for fixation, at least about 25% of the width of said fixation member is in one of the vertebral bodies and the remaining width of said fixation member is within said intervertebral body.

5. The stabilization device of claim 4, wherein said fixation member has a width and when positioned for fixation, about 25% to about 50% of the width of said fixation member is in one of the vertebral bodies and the remaining width of said fixation member is within said intervertebral body.

6. A stabilization device, comprising:

(a) an intervertebral body adapted for positioning between adjacent vertebral bodies, each vertebral body having a surface, said intervertebral body having a first end and a second end, and a first surface and a second surface for contacting the respective surfaces of the vertebral bodies, and further comprising a plate attached to said intervertebral body, said plate being adapted for fixation to at least one of the adjacent vertebral bodies; and (b) a fixation member adapted to fix said intervertebral body to one of the adjacent vertebral bodies, said fixation member being sized so that when positioned for fixation a portion of said fixation member extends beyond said first surface of said intervertebral body and engages the bone of the vertebral body, and wherein no portion of said fixation member extends beyond said second surface of said intervertebral body.

7. The stabilization device of claim 6, wherein said plate is adapted for fixation to the anterior or lateral sides of both of the adjacent vertebral bodies.

8. A method of stabilizing adjacent vertebral bodies, comprising the steps of:

(a) inserting an intervertebral body between the adjacent vertebral bodies, the intervertebral body having a first end and a second end, and a first surface and a second surface which contact the respective surfaces of the vertebral bodies, wherein the step of inserting an intervertebral body includes inserting an intervertebral body which includes a channel formed in at least one of the first and second surfaces; and (b) inserting at least one fixation member which is sized so that a portion of the fixation member extends beyond the first surface of the intervertebral body and engages one of the vertebral bodies, and such that no portion of the fixation member extends beyond the second surface of the intervertebral body.

9. The method of claim 8, wherein the step of inserting at least one fixation member includes inserting a fixation member which has a width and when positioned for fixation, at least about 25% of the width of the fixation member is in one of the vertebral bodies and the remaining width of the fixation member is within the intervertebral body.

10. The method of claim 9, wherein the step of inserting at least one fixation member includes inserting a fixation member which has a width and when positioned for fixation, about 25% to about 50% of the width of the fixation member is in one of the vertebral bodies and the remaining width of the fixation member is within the intervertebral body.

11. A method of stabilizing adjacent vertebral bodies, comprising the steps of:

(a) inserting an intervertebral body between the adjacent vertebral bodies, the intervertebral body having a first end and a second end, and a first surface and a second surface which contact the respective surfaces of the vertebral bodies, wherein the step of inserting an intervertebral body includes inserting an intervertebral body which includes a channel formed in at least one of the first and second surfaces, the channel extending longitudinally between the first and second ends of the intervertebral body, and (b) inserting at least one fixation member which is sized so that a portion of the fixation member extends beyond the first surface of the intervertebral body and engages one of the vertebral bodies, and such that no portion of the fixation member extends beyond the second surface of the intervertebral body.

12. A method of stabilizing adjacent vertebral bodies, comprising the steps of:

(a) inserting an intervertebral body between the adjacent vertebral bodies, the intervertebral body having a first end and a second end, and a first surface and a second surface which contact the respective surfaces of the vertebral bodies, and (b) inserting at least one fixation member which is sized so that a portion of the fixation member extends beyond the first surface of the intervertebral body and engages one of the vertebral bodies, and such that no portion of the fixation member extends beyond the second surface of the intervertebral body; and (c) further comprising the step of affixing a plate attached to the intervertebral body to the anterior or lateral side of at least one of the adjacent vertebral bodies.

13. The method of claim 12, wherein the step of affixing the plate includes affixing the plate to the anterior or lateral sides of both of the adjacent vertebral bodies.

14. A stabilization device, comprising an intervertebral body adapted for positioning between adjacent vertebral bodies each having a surface, said intervertebral body having a first end and a second, and a first surface and a second surface for contacting the respective surfaces of the vertebral bodies, said intervertebral body being constructed and arranged to allow said stabilization device to flex superiorly and inferiorly when arranged between the vertebral bodies after positioning of the intervertebral body between the vertebral bodies is complete and prior to fusion of the vertebral bodies; wherein said intervertebral body includes a plate adapted for fixation to the adjacent vertebral bodies, and legs extending transversely from said plate such that there is a space between said legs and to form an approximate U-shaped device, said legs including a slot to allow said stabilization device to flex superiorly and inferiorly when arranged between the vertebral bodies and prior to fusion of the vertebral bodies.

15. A stabilization device, comprising an intervertebral body adapted for positioning between adjacent vertebral bodies each having a surface, said intervertebral body having a first end and a second end, and a first surface and a second surface for contacting the respective surfaces of the vertebral bodies, said intervertebral body being constructed and arranged to allow said stabilization device to flex superiorly and inferiorly when arranged between the vertebral bodies after positioning of the intervertebral body between the vertebral bodies is complete and prior to fusion of the vertebral bodies, wherein said intervertebral body includes a plate adapted for fixation to the adjacent vertebral bodies, and legs extending transversely from said plate such that there is a space between said legs and to form an approximate U-shaped device, said legs being of different elasticity than said plate to allow said stabilization device to flex superiorly and inferiorly when arranged between the vertebral bodies and prior to fusion of the vertebral bodies.

16. The stabilization device of claim 15, wherein said legs are formed from polyethylene ether ketone (PEEK).

17. A method of stabilizing adjacent vertebral bodies each having anterior, lateral and posterior sides, comprising the step of:

inserting a stabilization device between adjacent vertebral bodies, the stabilization device having a first end and a second end, and a first surface and a second surface for contacting the vertebral bodies, the stabilization device being constructed and arranged to allow the stabilization device to flex superiorly and inferiorly when arranged between the vertebral bodies after positioning of the stabilization device between the vertebral bodies is complete and prior to fusion of the vertebral bodies, wherein the step of inserting the stabilization device includes inserting a stabilization device having a plate adapted for fixation to the adjacent vertebral bodies, and legs extending transversely from the plate such that there is a space between the legs and to form a U-shaped device, the legs including a slot extending transversely in a direction between anterior and posterior to allow the stabilization device to flex superiorly and inferiorly when arranged between the vertebral bodies and prior to fusion of the vertebral bodies.

18. A method of stabilizing adjacent vertebral bodies each having anterior, lateral and posterior sides, comprising the step of:

inserting a stabilization device between adjacent vertebral bodies, the stabilization device having a first end and a second end, and a first surface and a second surface for contacting the vertebral bodies, the stabilization device being constructed and arranged to allow the stabilization device to flex superiorly and inferiorly when arranged between the vertebral bodies after positioning of the stabilization device between the vertebral bodies is complete and prior to fusion of the vertebral bodies, wherein the step of inserting the stabilization device includes inserting a stabilization device having a plate adapted for fixation to the anterior or lateral sides of adjacent vertebral bodies, and legs extending transversely from the plate such that there is a space between the legs and to form an approximate U-shaped device, the legs being of different elasticity than the plate to allow the stabilization device to flex superiorly and inferiorly when arranged between the vertebral bodies and prior to fusion of the vertebral bodies.

19. The method of claim 18, wherein the step of inserting the stabilization device includes inserting a stabilization device having a plate and legs, wherein the legs are formed of polyether ether ketone (PEEK).

20. A method for reducing a displaced vertebra in a spine, comprising the steps of:

(a) providing a stabilization device having a plate adapted for fixation to adjacent vertebral bodies, and legs adapted for disposal between the adjacent vertebral bodies to provide support therebetween, there being a space between the legs such that the legs and the plate together define an approximate U-shape as viewed superior to inferior;

(b) positioning the stabilization device between a first vertebral body and a second vertebral body, the first vertebral body being in proper alignment with remaining vertebral bodies;

(c) attaching the device to the first vertebral body;

(d) reducing the second vertebral body by translating the second vertebral body so that it is in alignment with the first vertebral body; and (e) attaching the device to the second vertebral body.

21. A kit, comprising:

(a) at least one plate adapted for fixation to adjacent vertebral bodies, said plate having a front face and a back face, said plate extending along a plane, and (b) a plurality of separate and different stabilization members attachable to said plate, said stabilization members having a first surface and a second surface for contacting the vertebral bodies, which when affixed to said back face of said plate extend along a plane which is transverse to the plane of said plate.

22. A kit, comprising:

(a) a plurality of separate and different plates adapted for fixation to anterior or posterior sides of adjacent vertebral bodies, said plates having a front face and a back face and extending along a plane, and (b) at least one stabilization member having a first surface and a second surface for contacting the vertebral bodies, which when affixed to said back face of said plate extends along a plane which is transverse to the plane of said plate.

* * * * *